(12) United States Patent
Fukushima et al.

(10) Patent No.: US 8,354,278 B2
(45) Date of Patent: Jan. 15, 2013

(54) LIQUID FOR DISCHARGE, METHOD FOR DISCHARGING BIOSPECIMEN, AND COMPOUND

(75) Inventors: Hitoshi Fukushima, Tsukuba (JP); Yukihiro Hanaoka, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 12 days.

(21) Appl. No.: 12/986,567

(22) Filed: Jan. 7, 2011

(65) Prior Publication Data

US 2011/0177490 A1 Jul. 21, 2011

(30) Foreign Application Priority Data

Jan. 18, 2010 (JP) .................. 2010-008143
Dec. 24, 2010 (JP) .................. 2010-288654

(51) Int. Cl.
*G01N 33/48* (2006.01)
*C12Q 1/00* (2006.01)
*C07C 233/16* (2006.01)

(52) U.S. Cl. ................. 436/16; 435/4; 564/224; 554/64

(58) Field of Classification Search ........................ None
See application file for complete search history.

(56) References Cited

U.S. PATENT DOCUMENTS

2003/0091667 A1* 5/2003 Gormley et al. .............. 424/769
2010/0069290 A1 3/2010 Masada et al.

FOREIGN PATENT DOCUMENTS

| JP | A-2008-137967 | 6/2008 |
| JP | A-2009-250946 | 10/2009 |
| JP | A-2010-71846 | 4/2010 |

* cited by examiner

*Primary Examiner* — Shafiqul Haq
(74) *Attorney, Agent, or Firm* — Oliff & Berridge, PLC

(57) ABSTRACT

A liquid for discharge includes: a biospecimen; and at least one kind of compounds represented by the formula (1).

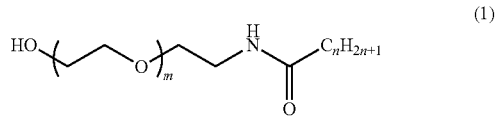

In the formula (1), $m \geq 8$, and $6 \leq n \leq 20$.

2 Claims, 3 Drawing Sheets

| | ref | C12P19 | C8P19 | C16P19 | P25(P177) | | ITEM NAME | ASSAY PRINCIPLE |
|---|---|---|---|---|---|---|---|---|
| LDH | 464 | 452 | 445 | 460 | 447 | 438 | LACTIC DEHYDROGENASE | ENZYME ACTIVITY ASSAY SPECTROMETRY (340nm) |
| AST | 191 | 182 | 183 | 189 | 185 | 185 | ASPARTATE AMINOTRASFERASE | ENZYME ACTIVITY ASSAY SPECTROMETRY (340nm) |
| ALT | 156 | 104 | 105 | 152 | 140 | 140 | ALANINE AMINOTRANSFERASE | ENZYME ACTIVITY ASSAY SPECTROMETRY (340nm) |
| ALP | 191 | 184 | 184 | 187 | 180 | 179 | ALKALINE PHOSPHATASE | ENZYME ACTIVITY ASSAY SPECTROMETRY |
| GGTP | 119 | 115 | 114 | 113 | 113 | 113 | GLUTAMYL TRASFERASE | ENZYME ACTIVITY ASSAY SPECTROMETRY |
| LAP | 28 | 27 | 27 | 28 | 27 | 27 | LEUCINE AMINOPEPTIDASE | ENZYME ACTIVITY ASSAY SPECTROMETRY |
| CK | 389 | 381 | 383 | 380 | 358 | 355 | CREATINE KINASE | ENZYME ACTIVITY ASSAY SPECTROMETRY (340nm) |
| CK-MB | 33 | 32 | 29 | 28 | 26 | 27 | CREATINE KINASE MB ISOENZYME | INHIBITION BY ANTI-S ANTIBODY + ENZYME ACTIVITY ASSAY |
| AMY | 497 | 485 | 484 | 486 | 475 | 469 | AMYLASE | ENZYME ACTIVITY ASSAY SPECTROMETRY |
| P-AMY | 283 | 277 | 276 | 277 | 271 | 268 | AMYLASE PANCREATIC ISOENZYME | INHIBITION BY ANTI-M ANTIBODY + ENZYME ACTIVITY ASSAY |
| CHE | 335 | 322 | 322 | 330 | 318 | 312 | CHOLINESTERASE | ENZYME ACTIVITY ASSAY SPECTROMETRY (340nm) |
| PL | 253 | 247 | 249 | 249 | 248 | 244 | PHOSPHOLIPID | ENZYMATIC SPECTROMETRY |
| T-CHO | 227 | 221 | 220 | 221 | 218 | 215 | TOTAL CHOLESTEROL | ENZYMATIC SPECTROMETRY |
| TG | 185 | 182 | 179 | 179 | 176 | 173 | TRIGLYCERIDE | ENZYMATIC SPECTROMETRY |
| HDL-C | 55 | 54 | 48 | 52 | 64 | 62 | HDL CHOLESTEROL | ENZYMATIC SPECTROMETRY |
| LDL-C | 111 | 107 | 106 | 109 | 103 | 102 | | ENZYMATIC SPECTROMETRY |
| UN | 56.2 | 54.6 | 55.0 | 55.1 | 55.6 | 54.7 | UREA NITROGEN | ENZYMATIC SPECTROMETRY (340nm) |
| UA | 8.8 | 8.6 | 8.6 | 8.6 | 8.7 | 8.4 | URIC ACID | ENZYMATIC SPECTROMETRY |
| CRE | 4.87 | 4.76 | 4.75 | 4.73 | 4.78 | 4.70 | CREATININE | ENZYMATIC SPECTROMETRY |
| GLU | 283 | 277 | 277 | 282 | 278 | 278 | GLUCOSE | ENZYMATIC SPECTROMETRY (340nm) |
| IP | 8.4 | 8.3 | 8.2 | 8.4 | 8.2 | 8.3 | INORGANIC PHOSPHORUS | ENZYMATIC SPECTROMETRY |
| Ca | 12.6 | 12.8 | 12.4 | 12.6 | 12.3 | 12.4 | CALCIUM | OCPC (CHELATE) METHOD SPECTROMETRY |
| Mg | 3.6 | 3.6 | 3.6 | 3.5 | 3.5 | 3.5 | MAGNESIUM | ENZYMATIC SPECTROMETRY (340nm) |
| T-BIL | 3.10 | 2.92 | 2.92 | 2.92 | 2.82 | 2.81 | TOTAL BILIRUBIN | ENZYMATIC SPECTROMETRY |
| D-BIL | 1.94 | 1.90 | 1.87 | 1.91 | 1.82 | 1.81 | DIRECT BILIRUBIN | ENZYMATIC SPECTROMETRY |
| TP | 7.1 | 7.0 | 7.0 | 7.1 | 6.9 | 6.9 | TOTAL PROTEIN | BIURET METHOD SPECTROMETRY |
| ALB | 4.4 | 4.3 | 4.3 | 4.2 | 4.2 | 4.2 | ALBUMIN | BCG METHOD SPECTROMETRY |
| CRP | 2.694 | 2.436 | 2.429 | 2.346 | 2.291 | 2.282 | CRP | NEPHELOMETRIC LATEX IMMUNOASSAY |
| Na | 142.4 | 138.9 | 138.3 | 140.7 | 139.4 | 139.2 | SODIUM | ION-SELECTIVE MEMBRANE ELECTRODE METHOD (DILUTION METHOD) |
| K | 6.25 | 6.01 | 6.02 | 6.16 | 6.06 | 6.06 | POTASSIUM | ION-SELECTIVE MEMBRANE ELECTRODE METHOD (DILUTION METHOD) |
| Cl | 120.7 | 112.7 | 117.1 | 118.6 | 117.1 | 117.3 | CHLORINE | ION-SELECTIVE MEMBRANE ELECTRODE METHOD (DILUTION METHOD) |

FIG. 1

|  | ref |  | C12P19 |  | C8P19 |  | C16P19 |  | P25(P1777) |  |
|---|---|---|---|---|---|---|---|---|---|---|
| LDH | 462.5 | 0.0 | 452 | -2.3 | 446 | -3.6 | 458.5 | -0.9 | 442.5 | -4.3 |
| AST | 176.5 | 0.0 | 182.5 | 3.4 | 188 | 6.5 | 189 | 7.1 | 185 | 4.8 |
| ALT | 156 | 0.0 | 104.5 | -33.0 | 149 | -4.5 | 151.5 | -2.9 | 140 | -10.3 |
| ALP | 190 | 0.0 | 184 | -3.2 | 188 | -1.1 | 187 | -1.6 | 179.5 | -5.5 |
| GGTP | 118 | 0.0 | 115 | -2.5 | 114.5 | -3.0 | 117.5 | -0.4 | 113 | -4.2 |
| LAP | 27.5 | 0.0 | 27 | -1.8 | 27 | -1.8 | 27.5 | 0.0 | 27 | -1.8 |
| CK | 388.5 | 0.0 | 382 | -1.7 | 375.5 | -3.3 | 380 | -2.2 | 356.5 | -8.2 |
| CK-MB | 32 | 0.0 | 30.5 | -4.7 | 31.5 | -1.6 | 28 | -12.5 | 26.5 | -17.2 |
| AMY | 497.5 | 0.0 | 484.5 | -2.6 | 484 | -2.7 | 486.5 | -2.2 | 472 | -5.1 |
| P-AMY | 283 | 0.0 | 276.5 | -2.3 | 275 | -2.8 | 277 | -2.1 | 269.5 | -4.8 |
| CHE | 336.5 | 0.0 | 322 | -4.3 | 327.5 | -2.7 | 330 | -1.9 | 315 | -6.4 |
| PL | 253 | 0.0 | 248 | -2.0 | 246.5 | -2.6 | 249 | -1.6 | 246 | -2.8 |
| T-CHO | 226.5 | 0.0 | 220.5 | -2.6 | 218 | -3.8 | 220 | -2.9 | 216.5 | -4.4 |
| TG | 183.5 | 0.0 | 178 | -3.0 | 178.5 | -2.7 | 179.5 | -2.2 | 174.5 | -4.9 |
| HDL-C | 54.5 | 0.0 | 48.5 | -11.0 | 52 | -4.6 | 69 | 26.6 | 63 | 15.6 |
| LDL-C | 111.5 | 0.0 | 106.5 | -4.5 | 108.5 | -2.7 | 106 | -4.9 | 102.5 | -8.1 |
| UN | 55.55 | 0.0 | 54.8 | -1.4 | 53.85 | -3.1 | 55.25 | -0.5 | 55.15 | -0.7 |
| UA | 8.8 | 0.0 | 8.6 | -2.3 | 8.6 | -2.3 | 8.65 | -1.7 | 8.5 | -3.4 |
| CRE | 4.87 | 0.0 | 4.755 | -2.4 | 4.725 | -3.0 | 4.76 | -2.3 | 4.74 | -2.7 |
| GLU | 283.5 | 0.0 | 277 | -2.3 | 275 | -3.0 | 282 | -0.5 | 278 | -1.9 |
| IP | 8.45 | 0.0 | 8.25 | -2.4 | 8.15 | -3.6 | 8.35 | -1.2 | 8.25 | -2.4 |
| Ca | 12.7 | 0.0 | 12.4 | -2.4 | 12.35 | -2.8 | 12.6 | -0.8 | 12.35 | -2.8 |
| Mg | 3.6 | 0.0 | 3.55 | -1.4 | 3.55 | -1.4 | 3.5 | -2.8 | 3.5 | -2.8 |
| T-BIL | 3.1 | 0.0 | 2.92 | -5.8 | 3.015 | -2.7 | 2.915 | -6.0 | 2.815 | -9.2 |
| D-BIL | 1.94 | 0.0 | 1.885 | -2.8 | 1.895 | -2.3 | 1.895 | -2.3 | 1.815 | -6.4 |
| TP | 7.1 | 0.0 | 7 | -1.4 | 6.95 | -2.1 | 7.1 | 0.0 | 6.9 | -2.8 |
| ALB | 4.4 | 0.0 | 4.3 | -2.3 | 4.3 | -2.3 | 4.2 | -4.5 | 4.2 | -4.5 |
| CRP | 2.7065 | 0.0 | 2.4325 | -10.1 | 2.6315 | -2.8 | 2.3495 | -13.2 | 2.2865 | -15.5 |
| Na | 142.35 | 0.0 | 138.6 | -2.6 | 138.9 | -2.4 | 140.75 | -1.1 | 139.3 | -2.1 |
| K | 6.25 | 0.0 | 6.015 | -3.8 | 6.035 | -3.4 | 6.165 | -1.4 | 6.06 | -3.0 |
| Cl | 120.95 | 0.0 | 114.9 | -5.0 | 117.15 | -3.1 | 118.7 | -1.9 | 117.2 | -3.1 |

FIG. 2

| ITEM | ITEM NAME | ADDITION AMOUNT 2% BY WEIGHT ref1 ASSAY DATA | DIFFERENCE (%) | C8P19 ASSAY DATA | DIFFERENCE (%) | C12P19 ASSAY DATA | DIFFERENCE (%) | C16P19 ASSAY DATA | DIFFERENCE (%) | ADDITION AMOUNT 3% BY WEIGHT ref2 ASSAY DATA | DIFFERENCE (%) | C8P19 ASSAY DATA | DIFFERENCE (%) | C12P19 ASSAY DATA | DIFFERENCE (%) | C16P19 ASSAY DATA | DIFFERENCE (%) |
|---|---|---|---|---|---|---|---|---|---|---|---|---|---|---|---|---|---|
| LDH | LACTIC DEHYDROGENASE | 462.5 | 0.0 | 446 | -3.6 | 452 | -2.3 | 458.5 | -0.9 | 455 | 0.0 | 449 | 1.32 | 450 | 1.10 | 450.5 | 0.99 |
| AST | ASPARTATE AMINOTRASFERASE | 176.5 | 0.0 | 188 | 6.5 | 182.5 | 3.4 | 189 | 7.1 | 193 | 0.0 | 191 | 1.04 | 182.5 | 5.44 | 191.5 | 0.78 |
| ALT | ALANINE AMINOTRANSFERASE | 156 | 0.0 | 149 | -4.5 | 104.5 | -33.0 | 151.5 | -2.9 | 152 | 0.0 | 144.5 | 4.03 | 85.5 | 43.75 | 146.5 | 3.62 |
| ALP | ALKALINE PHOSPHATASE | 190 | 0.0 | 188 | -1.1 | 184 | -3.2 | 187 | -1.6 | 193 | 0.0 | 189 | 0.00 | 189.5 | 1.81 | 189 | 2.07 |
| GGTP | α-GLUTAMYL TRASFERASE | 118 | 0.0 | 114.5 | -3.0 | 115 | -2.5 | 117.5 | -0.4 | 117 | 0.0 | 114.5 | 2.14 | 115.5 | 1.28 | 116.5 | 0.43 |
| LAP | LEUCINE AMINOPEPTIDASE | 27.5 | 0.0 | 27 | -1.8 | 27 | -1.8 | 27.5 | 0.0 | 31 | 0.0 | 31 | 0.00 | 30 | 3.23 | 30.5 | 1.61 |
| CK | CREATINE KINASE | 388.5 | 0.0 | 375.5 | -3.3 | 382 | -1.7 | 380 | -2.2 | 400 | 0.0 | 399 | 0.25 | 398.5 | 0.38 | 399.5 | 0.13 |
| CK-MB | CREATINE KINASE MB ISOENZYME | 32 | 0.0 | 31.5 | -1.6 | 30.5 | -4.7 | 28 | -12.5 | 38 | 0.0 | 37 | 2.63 | 35 | 7.89 | 33.5 | 11.84 |
| AMY | AMYLASE | 497.5 | 0.0 | 484 | -2.7 | 484.5 | -2.6 | 486.5 | -2.2 | 497 | 0.0 | 489 | 1.61 | 486 | 2.21 | 485.5 | 2.31 |
| P-AMY | AMYLASE PANCREATIC ISOENZYME | 283 | 0.0 | 275 | -2.8 | 276.5 | -2.3 | 277 | -2.1 | 283 | 0.0 | 278 | 1.77 | 277.5 | 1.94 | 276.5 | 2.30 |
| CHE | CHOLINESTERASE | 336.5 | 0.0 | 327.5 | -2.7 | 322 | -4.3 | 330 | -1.9 | 348 | 0.0 | 339.5 | 2.44 | 331 | 4.89 | 335.5 | 3.59 |
| PL | PHOSPHOLIPID | 253 | 0.0 | 246.5 | -2.6 | 248 | -2.0 | 249 | -1.6 | 260 | 0.0 | 252.5 | 2.88 | 252.5 | 2.88 | 251.5 | 3.27 |
| T-CHO | TOTAL CHOLESTEROL | 226.5 | 0.0 | 218 | -3.8 | 220.5 | -2.6 | 220 | -2.9 | 229 | 0.0 | 223.5 | 2.40 | 221.5 | 3.28 | 221.5 | 3.28 |
| TG | TRIGLYCERIDE | 183.5 | 0.0 | 178.3 | -3.0 | 178 | -3.0 | 179.5 | -2.2 | 184 | 0.0 | 179 | 2.72 | 178 | 3.26 | 179.5 | 2.45 |
| HDL-C | HDL CHOLESTEROL | 54.5 | 0.0 | 52 | -4.6 | 48.5 | -11.0 | 69 | 26.6 | 54 | 0.0 | 54 | 3.57 | 50.5 | 9.82 | 71 | 26.79 |
| LDL-C | LDL CHOLESTEROL | 111.5 | 0.0 | 106.5 | -4.5 | 106.5 | -4.5 | 106 | -4.9 | 107 | 0.0 | 106 | 0.93 | 104 | 2.80 | 101.5 | 5.14 |
| UN | UREA NITROGEN | 55.55 | 0.0 | 53.85 | -3.1 | 54.8 | -1.4 | 55.25 | -0.5 | 56.4 | 0.0 | 55.25 | 2.04 | 55.65 | 1.33 | 56.1 | 0.53 |
| UA | URIC ACID | 8.8 | 0.0 | 8.6 | -2.3 | 8.6 | -2.3 | 8.65 | -2.3 | 9 | 0.0 | 8.8 | 2.22 | 8.8 | 2.22 | 8.8 | 2.22 |
| CRE | CREATININE | 4.87 | 0.0 | 4.725 | -3.0 | 4.755 | -2.4 | 4.76 | -2.3 | 4.98 | 0.0 | 4.9 | 1.61 | 4.885 | 1.91 | 4.915 | 1.31 |
| GLU | GLUCOSE | 283.5 | 0.0 | 275 | -3.0 | 277 | -2.3 | 282 | -0.5 | 283 | 0.0 | 278.5 | 1.59 | 280 | 1.06 | 279 | 1.41 |
| IP | INORGANIC PHOSPHORUS | 8.45 | 0.0 | 8.15 | -3.6 | 8.25 | -2.4 | 8.35 | -1.2 | 8.4 | 0.0 | 8.1 | 3.57 | 8.15 | 2.98 | 8.15 | 2.98 |
| Ca | CALCIUM | 12.7 | 0.0 | 12.35 | -2.8 | 12.4 | -2.4 | 12.6 | -0.8 | 12.9 | 0.0 | 12.6 | 2.33 | 12.7 | 1.55 | 12.85 | 0.39 |
| Mg | MAGNESIUM | 3.6 | 0.0 | 3.55 | -1.4 | 3.55 | -1.4 | 3.5 | -2.8 | 3.4 | 0.0 | 3.4 | 0.00 | 3.45 | -1.47 | 3.4 | 0.00 |
| T-BIL | TOTAL BILIRUBIN | 3.1 | 0.0 | 3.015 | -2.7 | 2.92 | -5.8 | 2.915 | -6.0 | 3.23 | 0.0 | 3.205 | 0.77 | 3.12 | 3.41 | 3.135 | 2.94 |
| D-BIL | DIRECT BILIRUBIN | 1.94 | 0.0 | 1.895 | -2.3 | 1.895 | -2.3 | 1.895 | -2.3 | 2.01 | 0.0 | 1.965 | 2.24 | 1.97 | 1.99 | 1.97 | 1.99 |
| TP | TOTAL PROTEIN | 7.1 | 0.0 | 6.95 | -2.1 | 7 | -1.4 | 7.1 | 0.0 | 7.2 | 0.0 | 7.05 | 2.08 | 7.1 | 1.39 | 7.1 | 1.39 |
| ALB | ALBUMIN | 4.4 | 0.0 | 4.3 | -2.3 | 4.3 | -2.3 | 4.2 | -4.5 | 4.5 | 0.0 | 4.4 | 2.22 | 4.4 | 2.22 | 4.3 | 4.44 |
| CRP | CRP | 2.7065 | 0.0 | 2.6315 | -2.8 | 2.4325 | -10.1 | 2.3495 | -13.2 | 2.694 | 0.0 | 2.6465 | 1.76 | 2.469 | 8.35 | 2.3555 | 12.55 |
| Na | SODIUM | 142.35 | 0.0 | 138.9 | -2.4 | 138.6 | -2.6 | 140.75 | -1.1 | 142.6 | 0.0 | 140.25 | 1.65 | 149.55 | -4.87 | 140.7 | 1.33 |
| K | POTASSIUM | 6.25 | 0.0 | 6.035 | -3.4 | 6.015 | -3.8 | 6.165 | -1.4 | 6.23 | 0.0 | 6.04 | 3.05 | 6.04 | 3.05 | 6.07 | 2.57 |
| Cl | CHLORINE | 120.95 | 0.0 | 117.15 | -3.1 | 114.9 | -5 | 118.7 | -1.9 | 119.8 | 0.0 | 117.15 | 2.21 | 117 | 2.34 | 117.25 | 2.13 |

FIG. 3

LIQUID FOR DISCHARGE, METHOD FOR DISCHARGING BIOSPECIMEN, AND COMPOUND

The entire disclosure of Japanese Patent Application No 2010-008143, filed Jan. 18, 2010 is expressly incorporated by reference herein.

BACKGROUND

1. Technical Field

The present invention relates to a liquid for discharge, a method for discharging a biospecimen, a compound, and the like.

2. Related Art

In the current state, several tens of cubic centimeters of blood is required in order to perform tests on dozens of biomolecules contained in blood. Therefore, a detection technique in which the amount of blood required for the tests is drastically reduced is demanded.

It is considered that an ink jet technique can be used as a method of dispensing a trace of liquid in an accurate and efficient manner. For instance, JP-A-2008-137967 discloses an example of discharging a solution which includes at least one of proteins and peptides by an ink jet method using thermal energy.

Biospecimens, such as blood, contain a lot of molecules including proteins, which are prone to be nonspecifically adsorbed around a discharge port of an ink jet head or on the surface of a flow path. Consequently, in some cases, the adhesion of these molecules results in clogging of the discharge port or the flow path, and thus it is impossible to stably perform the discharge. Moreover, since biochemical tests are performed on the discharged biospecimen, it is necessary to maintain biological activity of biomolecules contained in the specimen. However, JP-A-2008-137967 does not disclose specific solutions to the problem.

SUMMARY

An advantage of some aspects of the invention is to provide a liquid for discharge which includes a biospecimen and can be stably discharged from a fine discharge port without decreasing biological activity of biomolecules.

A liquid for discharge according to an aspect of the invention includes a biospecimen and at least one of compounds represented by formula (1) in which $m \geq 8$, and $6 \leq n \leq 20$.

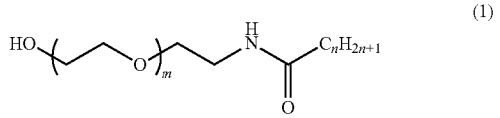
(1)

With such a configuration, it is possible to prevent the molecules such as proteins contained in the biospecimen from adhering around a discharge port of an ink jet head or on the surface of a flow path and clogging the discharge port or the flow path, and to stably perform the discharge accordingly. Also, even when the compound is added to the biospecimen, it is possible to obtain a high reproducibility of biochemical reactions without decreasing the biological activity of biomolecules contained in the biospecimen.

It is preferable that the compound is contained in an amount of 2% by weight or more based on the biospecimen.

With such a configuration, it is possible to obtain sufficient stability of discharge even long after the liquid for discharge is filled in the ink jet head.

In the formula (1), it is preferable that $m \geq 16$, and $n=8$.

With such a configuration, it is possible to obtain sufficient stability of discharge even long after the liquid for discharge is filled in the ink jet head.

It is preferable that the biospecimen contain serum.

With such a configuration, it is possible to drastically reduce the required amount of blood to be taken for the tests.

A method for discharging a biospecimen, according to another aspect of the invention includes adding at least one kind of the compounds represented by the formula (1) to the biospecimen, and discharging the biospecimen by using an ink jet method.

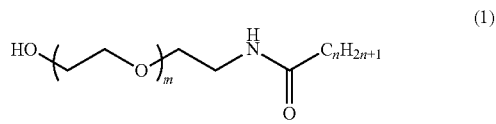
(1)

(In the formula (1), $m \geq 8$, and $6 \leq n \leq 20$.)

With such a configuration, it is possible to prevent the molecules such as proteins contained in the biospecimen from adhering around a discharge port of an ink jet head or on the surface of a flow path and clogging the discharge port or the flow path, and to stably perform the discharge accordingly. Also, even when the compound is added to the biospecimen, it is possible to obtain a high reproducibility of biochemical reactions without decreasing the biological activity of biomolecules contained in the biospecimen.

A compound according to still another aspect of the invention is represented by the formula (1) and can be added to the biospecimen so as to be discharged using the ink jet method. The compound includes the following structure.

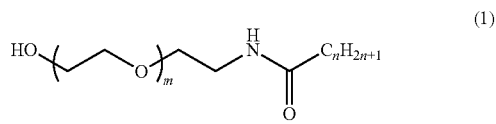
(1)

(in the formula (1), $m \geq 8$, and $6 \leq n \leq 20$.)

By adding the compound represented by the formula (1) to the biospecimen, it is possible to prevent the molecules such as proteins contained in the biospecimen from adhering around a discharge port of an ink jet head or on the surface of a flow path and clogging the discharge port or the flow path, and to perform stable discharge accordingly. Also, even when the compound is added to the biospecimen, it is possible to obtain a high reproducibility of biochemical reactions without decreasing the biological activity of biomolecules contained in the biospecimen.

BRIEF DESCRIPTION OF THE DRAWINGS

The invention will be described with reference to the accompanying drawings, wherein like numbers reference like elements.

FIG. 1 is a table showing assay results of biochemical reaction activities of serum protein molecules contained in the liquid for discharge according to an embodiment of the invention.

FIG. 2 is a table showing assay results of biochemical reaction activities of serum protein molecules contained in the liquid for discharge according to an embodiment of the invention.

FIG. 3 is a table showing assay results of biochemical reaction activities of serum protein molecules after discharge, obtained when the amount of the compound to be added was changed.

DESCRIPTION OF EXEMPLARY EMBODIMENTS

Hereinafter, an embodiment of the invention will be described.

The liquid for discharge according to an embodiment of the invention can be obtained by adding a compound to a biospecimen. The compound to be added is represented by the following formula (1). The compound (1) is an ethylene glycol-based surfactant molecule with a linear structure represented by E-P-K, wherein E is an ethylene glycol chain, P is a peptide bond chain (CONH), and K is an alkyl chain.

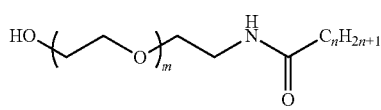
(1)

The compound (1) includes an ethylene glycol chain with a chain length of m, and an alkyl chain with a chain length of n, in which $m \geq 8$ and $6 \leq n \leq 20$. Particularly, it is preferable that $m \geq 16$, and $n=8$.

Examples of the biospecimen include blood and serum. Herein, a human serum sample CRPII (a sample in which a C-reactive protein is added to human serum to yield a certain concentration) is used.

Table 1 shows an example of the compound (1).

TABLE 1

| Compound Name | Manufacturer | Structural detail |
|---|---|---|
| C8P19 | Polypure | n = 8, m = 19 |
| C12P19 | Polypure | n = 12, m = 19 |
| C16P19 | Polypure | n = 16, m = 19 |

Next, an example of a synthesis method of the compound (1) will be described.

10 mmol of a fatty acid chloride is dissolved in 50 ml of dichloromethane, and 12 mmol of N-hydroxysuccinimide is added thereto, followed by stirring. After 2 ml of triethylamine is further added thereto, the mixture is stirred at room temperature for 30 minutes (formula (2)). Subsequently, 11.1 mmol of monoamino PEG19 (molecular weight: 898.1, manufactured by Polypure) is added to the mixture at a time, followed by further stirring. When it is confirmed, by HPLC or the like, that about 90% of monoamino PEG19 added is consumed, the reaction mixture is mixed so that the reaction mixture becomes 5% based on 50 ml of HCl, followed by stirring for a while. In extraction, an organic layer is washed with water a couple of times, and then vacuum concentration of the organic layer is performed to remove dichloromethane. Diethylether is added to the residue, decantation is performed a couple of times, and then the resultant is dried to obtain a white solid (formula (3)). The yield of the compound (1) is 75 to 90%.

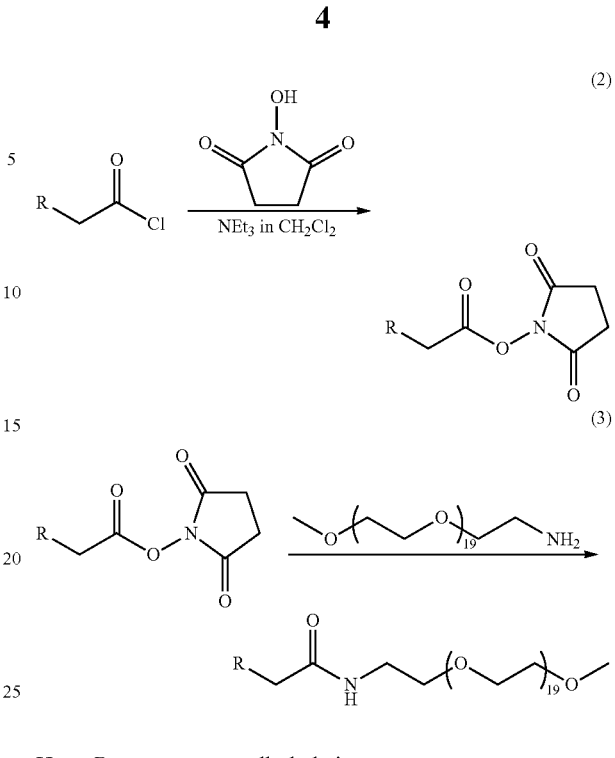

Here, R represents an alkyl chain.

Next, a production method of the liquid for discharge according to the embodiment of the invention will be described. Herein, description will be made of a case of using serum as the biospecimen, as an example.

First, to a human serum sample CRPII (a sample in which a C-reactive protein is added to human serum to yield a certain concentration), the compound (1) is added and the compound (1) is dissolved in the serum while avoid shaking as much as possible. The amount of the compound (1) to be added is preferably 2% by weight or more based on the serum solution. Dissolution is performed at room temperature. Alternatively, dissolution may be performed by immersing the container in water warmed to 35° C., and dissolving the compound (1) while gently moving the container. By this operation, it is possible to speed up the dissolution.

After the dissolution, precipitated insoluble fractions are removed, and the solution is stored at 5° C. for half a day.

Next, the liquid for discharge according to the embodiment of the invention is filled in the ink jet head to perform discharge.

FIGS. 1 and 2 are tables showing assay results of the biochemical reaction activities of serum protein molecules after discharge. FIGS. 1 and 2 show assay values obtained from an assay performed for only the serum sample as reference assay data (ref), and an assay value obtained from an assay performed for serum samples to which one of C12P19, C8P19, C16P19 and P25 is added (P1777, Tokyo Chemical Industry Co., Ltd.). Incidentally, while the serum for assaying the reference assay data is not discharged from the ink jet head, the serum for assaying other data is discharged from the ink jet head for the assay. FIG. 1 shows two assay values of the actual biochemical reaction activities per serum, and FIG. 2 shows differences (%) between average values of respective assay data in FIG. 1 and reference assay data. When the difference from the reference assay data is 10% or more, it is indicated in bold type.

P25 (P1777) is a compound represented by the following formula (4), and unlike the compound (1), P25 is an ethylene glycol surfactant molecule with a structure which does not include a peptide bond chain (CONH) between an ethylene glycol chain and an alkyl chain.

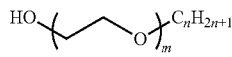 (4)

Here, n=12, and 5<m<30.

As shown in FIG. 2, it was found that, when a compound with a short alkyl chain (in which n is small) is added, the bioactivity of the protein in serum is more effectively maintained. Particularly, when C8P19 is added in an amount of 2% by weight or more, a high reproducibility of the biochemical reactions was obtained in almost every protein test item.

C12P19 and C16P19 also showed a high reproducibility of biochemical reactions except for some proteins such as ALT and CRP. It was found that, P25 (P1777) also showed a high reproducibility of biochemical reactions except for some proteins, but C12P19, C8P19, and C16P19 were more effective in maintaining the bioactivity of proteins in serum.

Serum contains lots of molecules such as proteins which are prone to be adsorbed nonspecifically around the discharge port of the ink jet head or the surface of the flow path; therefore, as a result of the adhesion of these molecules, the discharge port or the flow path is clogged in some cases. In addition, as the serum solution is dried and coagulated over time, the discharge port or the flow path is clogged accordingly. According to the liquid for discharge of the embodiment of the invention, by adding 2% by weight or more of the compound represented by the formula (1) to the serum or the like, it is possible to prevent the protein contained in serum from adhering around the discharge port of the ink jet head or the surface of the flow path and clogging the discharge port or the flow path, and to perform stable discharge. When the amount of the compound to be added is smaller than 2% by weight, the stability of the discharge is insufficient.

As described so far, by adding 2% by weight or more of the compound represented by the formula (1) to the serum or the like, it is possible to prevent the protein contained in serum from adhering around the discharge port of the ink jet head or the surface of the flow path and clogging the discharge port or the flow path, and thereby the liquid for discharge according to the embodiment of the invention can be stably discharged.

Also, even when the compound is added to the serum, the high reproducibility of the biochemical reaction is obtained without decreasing the bioactivity of the biomolecule in the serum except for some proteins.

Furthermore, the shorter the length of the alkyl chain contained in the molecule of the compound represented by the formula (1) (the smaller the n), the higher the effect of maintaining the bioactivity of the protein in the serum.

According to the embodiment of the invention, as the compound (1), an ethylene glycol-based surfactant molecule with a linear structure represented by E-P-K, wherein E is an ethylene glycol chain, P is a peptide bond chain (CONH), and K is an alkyl chain is used. However, for example, the compound (1) may be a molecule having a branched structure such as (E-P) 2-K (a molecule in which each of two hydrogen atoms binding to carbon of the alkyl chain K is substituted with (E-P)) or (E-P) 3-K (a molecule in which each of three hydrogen atoms binding to carbon of the alkyl chain K is substituted with (E-P)).

FIG. 3 is a table showing the assay results of the biochemical reaction activities of the serum protein molecules after discharge, obtained when the amount of the compound to be added was changed. The table shows the assay values obtained by assaying only the serum sample as reference assay data (ref 1 and ref 2), and the assay values obtained by assaying respective serum samples to which one of C8P19, C12P19, and C16P19 is added in an amount of 2% by weight or 3% by weight. It was impossible to discharge the serum for assaying the reference assay data (the addition amount of the surfactant compound: 0% by weight) from the ink jet head. The respective serum samples containing 2% by weight or 3% by weight of C8P19, C12P19, or C16P19 were discharged from the ink jet head, and then the serum samples were recovered and subjected to the assay. The assay was performed twice, and a column of difference (%) shows the differences between average values of respective assay data and reference assay data as percentages. Whether the difference is within ±10% with respect to each item in terms of the test is an index of determining whether the assay method can be used practically.

As shown in FIG. 3, it can be found that, when C8P19 is added in amounts of 2% by weight and 3% by weight, the difference in each item is within ±10%. Accordingly, it can be seen that, by adding C8P19 in an amount of 2% by weight or more, it is possible to perform the discharge and the practical biochemical test of a trace biospecimen using an ink jet technique while maintaining the bioactivity of biomolecules. It can be also seen that by adding respective surfactant additives in an amount of 2% by weight or more, it is possible to perform more stable discharge by means of a piezoelectric ink jet system.

What is claimed is:

1. A liquid for discharge comprising:
at least one of blood or blood serum, and at least a compound represented by the formula (1):

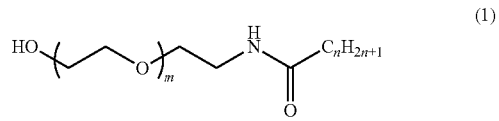 (1)

wherein m≧8, and 6≦n≦20, and
wherein the compound is contained 2% by weight or more of the at least one of the blood or the blood serum.

2. The liquid for discharge according to claim 1, wherein m≧16 and n=8.

* * * * *